US005729167A

United States Patent [19]

Kujawa et al.

[11] Patent Number: 5,729,167

[45] Date of Patent: Mar. 17, 1998

[54] LOW POWER CONSUMPTION SWITCH INTERFACE CIRCUIT

[75] Inventors: Gregory A. Kujawa, St. Charles; Paul Moraghan, Chicago; Eugene L. Wineinger, Carol Stream, all of Ill.

[73] Assignee: Motorola, Inc., Schaumburg, Ill.

[21] Appl. No.: 595,324

[22] Filed: Feb. 1, 1996

[51] Int. Cl.$^6$ .................. A01H 1/60

[52] U.S. Cl. .................. 327/137; 327/108; 327/135; 307/137; 307/141.4

[58] Field of Search .................. 327/538, 72, 170, 327/374, 376, 389, 391, 377, 135, 137, 108; 326/87; 307/131, 135, 137, 141, 141.4

[56] References Cited

U.S. PATENT DOCUMENTS

| | | | |
|---|---|---|---|
| 3,794,850 | 2/1974 | Hirose | 307/137 |
| 4,975,598 | 12/1990 | Borkar | 326/121 |
| 5,258,654 | 11/1993 | Roberts et al. | 307/137 |
| 5,289,051 | 2/1994 | Zitta | 327/108 |
| 5,523,633 | 6/1996 | Imaizumi et al. | 307/137 |

*Primary Examiner*—Margaret Rose Wambach
*Assistant Examiner*—Terry L. Englund
*Attorney, Agent, or Firm*—Nicholas Hopman

[57] ABSTRACT

A low power consumption switch interface circuit (100) includes a current source (109) for providing switch current (144) having a magnitude dependent on a state of a current range signal (135). An input terminal (142) is provided to conduct the switch current (144) to an external switch (102). A circuit (101, 103, 119) for detecting a signal (141) present at the input terminal (142) provides a measured pulse (127) when the signal (141) is detected. A current range selector (129), coupled to the current source (109), outputs a first state of the current range signal (135) while the measured pulse (127) is outputted from the circuit (101, 103, 119), and a second state of the current range signal (135) while the measured pulse (127) is not outputted from the circuit (101, 103, 119). The current source (109) provides the switch current (144) at a first magnitude responsive to the first state of the current range signal (135), and a second magnitude responsive to the second state of the current range signal (135).

4 Claims, 1 Drawing Sheet

LOW POWER CONSUMPTION SWITCH INTERFACE CIRCUIT

FIELD OF THE INVENTION

This invention is generally directed to the field of switch interface circuits, and specifically for a low power consumption application.

BACKGROUND OF THE INVENTION

Certain applications that need to measure electromechanical switch activations need to operate at a very low level of power consumption. Often these applications are powered by a battery and need to conserve energy to ensure a long service life for the equipment.

Electromechanical switches however often require a relatively high level of power consumption to ensure reliable operation. For instance, the physical contacts of these electromechanical switches often can be contaminated with a resistive substance. To sense the switch's actuation preferably, an electrical potential of relatively high voltage must be applied across the switch's contaminated contacts to enable current flow which then can be sensed. Since a relatively high voltage must be applied, once the contact contamination has been overcome, the magnitude of the current flowing through the switch will be relatively significant. This current that flows through the switch's contacts is often referred to as a "wetting current". Since power consumption is directly a product of the applied voltage and the conducting current it too will be relatively high. As long as the switch is conducting current the significant power loss will occur.

What is needed is an improved switch interface circuit that reliably detects electromechanical switch closure while minimizing the power consumption.

SUMMARY OF THE INVENTION

Figure 1:
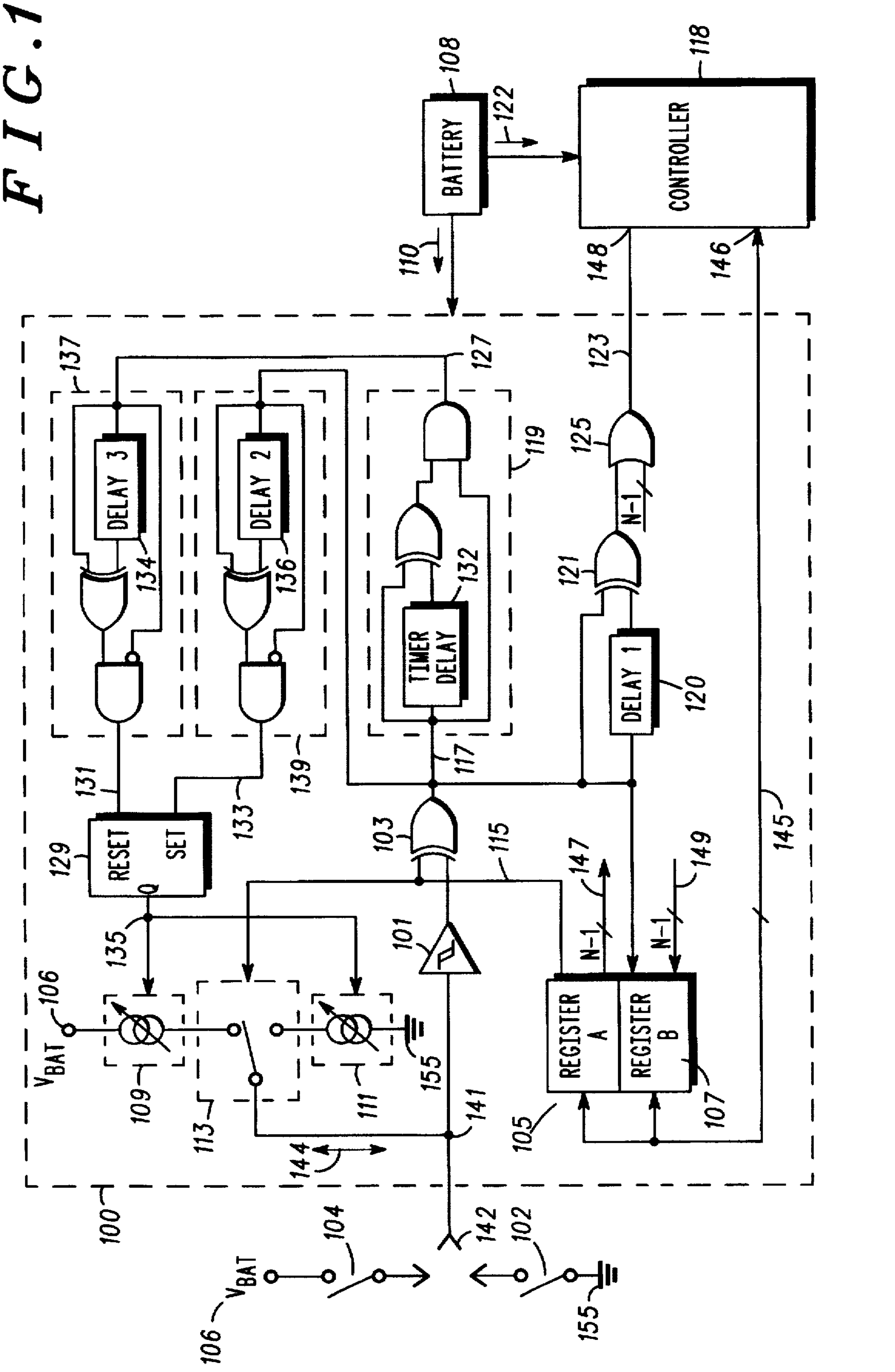
FIG. 1 is a schematic block diagram in accordance with a preferred embodiment of the invention.

A low power consumption switch interface circuit includes a current source for providing switch current having a magnitude dependent on a state of a current range signal. An input terminal is provided to conduct the switch current to an external switch. A circuit for detecting a signal present at the input terminal provides a measured pulse when the signal is detected. A current range selector outputs a first state of the current range signal while the measured pulse is outputted from the circuit and a second state of the current range signal, while the measured pulse is not outputted from the circuit. The current source provides the switch current at a first magnitude responsive to the first state of the current range signal, and a second magnitude responsive to the second state of the current range signal. Essentially, the low power consumption switch interface circuit will provide a relatively high magnitude "wetting current" to the external switch to clear any contact contamination. Once the contamination is cleared, and the switch state is electrically sensed, the low power consumption switch interface circuit reduces the switch current to a relatively low magnitude current to minimize current consumption—thus battery drain.

Further features of the low power consumption switch interface circuit include provision for either a high-side or a low-side external switch interface. The preferred embodiment will be better understood by viewing a system block diagram shown in FIG. 1.

DETAILED DESCRIPTION OF A PREFERRED EMBODIMENT

In the preferred embodiment a low-side switch application will be detailed. A low power consumption switch interface circuit 100 provides for interfacing to multiple external switches. For simplicity details of only one switch interface are shown. The low power consumption switch interface circuit 100 is powered by a battery 108, and has external low-side switch 102 connected between circuit ground 155 and an input terminal 142. Alternatively, in a high-side switch application, an external high-side switch 104 is connected between Vbat 106 and the input terminal 142. Current 110 is consumed at a rate dependent on the low power consumption switch interface circuit's 100 operating mode. Essentially, the approach used here is to minimize power consumption by only allowing a relatively high current drain from the battery 108 when a switch initially closes—so that any contamination on the switch's contacts can be cleared. A short time later, when the switch state is determined, the low power consumption switch interface circuit 100 reduces this relatively high "wetting current" to a relatively low current—thus conserving the battery's power. The relatively low current in the preferred embodiment is preferably about 1 milliamp. This approach offers a significant advantage over prior art schemes which continually depleted a battery by sourcing a "wetting current" as long as an associated switch contact was closed—rather than terminating the provision of the "wetting current" after the switch state has been measured as in the present embodiment.

A variable current source 109, or a variable current sink 111 in a high-side switch application, is initially configured to provide (source in the low-side switch application, and sink in the high-side switch application) a switch current 144 that is relatively high. Note that the direction of current flow is dependent on whether the application uses a high-side or a low-side switch. This relatively high switch current 144 is typically in the range of 10–50 milliamps, but may be configured outside of this range. The actual magnitude of switch current 144 conductible through the input terminal 142 through the low-side switch 102 is controlled by the variable current source 109 and/or the variable current sink 111, in accordance with a current range signal 135, output from a current range selector, in this case a flip-flop 129. To effect the selection of the relatively high switch current 144, the current range signal 135 is initialized to a logical "1" state when the low power consumption switch interface circuit 100 is powered up. Note that later, after the low-side switch actuation is sensed (which requires the low-side switch 102 to be closed), the current range signal 135 will be forced to a logical "0" state which will cause the variable current source 109 to reduce its output (switch) current 144 to a relatively low magnitude to reduce current consumption of the switch interface circuit 100—thus conserve power drain from the battery 108.

Another application configurable part of the low power consumption switch interface circuit 100, is a high-side/low-side selection switch 113. The high-side/low-side selection switch 113 is configured by a high-side/low-side selection signal 115 to conduct the switch current 144, dependent on the type of switch used in the particular application. The high-side/low-side selection signal 115 is provided from register A 105 which is a register programmable via a serial data link 145 driven by a controller 118. Alternatively another data link type could be applied. In the preferred embodiment the low power consumption switch interface circuit 100 is integrated onto a custom integrated circuit. This custom integrated circuit is used to interface to many switches, each of which may be configured in a high-side or a low-side switch arrangement. Register A 105 embodies a high-side/low-side selection signal 147 for each of the remaining (N-1) switches on the low power consumption switch interface circuit 100. All circuits embodied within the low power consumption switch interface circuit 100 except 105, 107, and 125, are replicated for each on N input terminals 142—thus for each input switch.

Preferably the controller 118 is constructed using a Motorola MC68HC05 type microcontroller. Conveniently the Motorola MC68HC05 has a built-in serial data link, dubbed a SPI (Serial Peripheral Interface) 146. Also, the Motorola MC68HC05 can be operated in a low power consumption mode. The Motorola MC68HC05 can be brought out of the low power consumption mode via an interrupt received at an interrupt input 148. Once interrupted the Motorola MC68HC05 can actively interrogate the low power consumption switch interface circuit 100 to read the state of switches as well as configure the low power consumption switch interface circuit 100 for various switch applications. Alternatively, the controller 118 can be constructed using another microcontroller, or other logic based circuit as desired.

In operation, when the low-side switch 102 is actuated closed, a switch current 144 flows from Vbat 106, regulated by the variable current source 109, through the input terminal 142, through the low-side switch 102, to circuit ground 155. If the low-side switch 102 has any contamination built up on its contacts, this contamination will be broken down by the relatively high voltage Vbat 106. When this happens, the switch current 144 will flow, and as mentioned above, at a relatively high source current, in the preferred case 10–50 milliamps. Before the low-side switch 102 is actuated closed, a signal, here measured as a voltage 141 present at the input terminal 142, will have a magnitude substantially equal to Vbat 106. This voltage 141 is sensed by a Schmitt trigger 101. The Schmitt trigger 101 has built-in hysteresis limits which act to debounce the low-side switch's modulation of the voltage present at the input terminal 142. When the low-side switch 102 is actuated closed, the magnitude of the voltage 141 present at the input terminal 142 will fall from Vbat 106 to approximately circuit ground 155 potential. This change in state of the voltage 141 is sensed by a change-in-state detector, or gate 103. The gate 103 is applied to selectively provide a sensed switch signal 117 dependent on the state of the high-side/low-side selection signal 115 provided by register A 105, to register B 107. Register B 107 essentially latches the state of the low-side switch 102. This state is later readout of register B 107 by the controller 118 over the serial data link 145.

With the mission of clearing a contaminated switch accomplished, the next requirement is to readout the switch's state and then to minimize the current drain, thus the power consumption, of the switch interface circuit 100. To sense the switch's change in state, an edge detector, or interrupt generation circuit, comprised of circuits 120 and 121, provides an interrupt signal 123 dependent on a gate 125. Block 120, DELAY1 is set to 10 microseconds which should be sufficient to interrupt the controller 118. Note that gate 125 also collects input from the N-1 other input circuits. The interrupt signal 123 wakes up the controller via the interrupt input 148.

Once the controller 118 is awake it starts consuming a relatively high amount of current 122 from the battery 108. The controller 118 then reads the state of the low-side switch 102 captured in register B 107 via serial data link 145. Once read the controller 118 powers down to consume a relatively low amount of current 122 from the battery 108. Meanwhile, the low power consumption switch interface circuit 100 is still consuming current at a relatively low level.

Concurrent with the transition of the sensed switch signal 117, a positive edge triggered one-shot circuit 119 is actuated. The positive edge triggered one-shot circuit 119 outputs a measured pulse, or signal 127 that transitions high when the sensed switch signal 117 transitions high—indicating that the low-side switch 102 has closed. 10 milliseconds later, as determined by the TIMER DELAY block 132, the signal 127 transitions back low. Depending on the type of contact used in switch 102 the TIMER DELAY block 132 may have a different time out. This low transition activates circuit 137. Circuit 137 is a falling-edge triggered one-shot. 10 microseconds seconds later, as determined by a DELAY 3 block 134, a reset signal 131 activates a reset state of the flip-flop 129. This action in turn will force the current range signal 135 to a logical "0" state, which will cause the variable current source 109 to reduces its output (switch) current 144 to a relatively low magnitude to reduce current consumption of the switch interface circuit 100—thus conserve power consumption 110 from the battery 108. Essentially, the TIMER DELAY block 132 is a period set long enough to ensure that a relatively high "wetting current" flows through the low-side switch 102 to clear the contact, and have the low-side switch 102 closed state detected by the controller 118, and short enough so as not to excessively deplete the battery 108.

Next, when the low-side switch 102 opens, the voltage 141 present at the input terminal 142 will return to Vbat 106. As described before, this voltage 141 is sensed by a Schmitt trigger 101. This change in state of the voltage 141 is sensed by the gate 103. As described earlier the gate 103 will selectively provide the sensed switch signal 117 dependent on the state of the high-side/low-side selection signal 115 provided by register A 105, to register B 107. In this case a logical "0" state will be recorded in register B 107 indicating that the low-side switch 102 has been opened. Through the action of the earlier-described circuit including elements 120, 121, and 125 another interrupt signal 123 wakes up the controller 118. As before the controller 118 reads the state of the low-side switch 102 reflected in register B 107.

Concurrent with the falling transition of the switch signal 117, another falling-edge triggered one-shot 139 is activated. 10 microseconds seconds later, as determined by a DELAY 2 block 136, a set signal 133 reactivates the set state of the flip-flop 129. This action in turn will force the current range signal 135 to a logical "1" state, which will cause the variable current source 109 to increase its output (switch) current 144 to a relatively high magnitude—thus rearming the switch interface circuit 100 in case the low-side switch 102 is actuated closed. While the low-side switch 102 remains open the current 110 consumed by the switch interface circuit 100 remains low because the switch current 144 has no path to ground 155.

In conclusion, an improved switch interface circuit has been detailed. The improved switch interface circuit reliably detects electromechanical switch closure while minimizing the power consumption. This approach is a significant improvement over prior art schemes which continually depleted a battery by sourcing a "wetting current" as long as an associated switch contact was closed. The described approach only allows the relatively high switch "wetting current" to conduct until the switch's state has been detected. Furthermore, this approach can be easily integrated onto an integrated circuit to reduce component count-thereby increasing system reliability.

What is claimed is:

1. A low power consumption switch interface circuit comprising:

a current source for providing switch current having a magnitude dependent on a state of a current range signal;

an input terminal for conducting the switch current provided by the current source through a switch;

a change-of-state detector for detecting a voltage present at the input terminal, and for providing a sensed switch signal having a state dependent on a magnitude of the voltage;

an interrupt generation circuit for generating an interrupt signal dependent on the sensed switch signal;

a timer that outputs a measured pulse, triggered by the sensed switch signal; and a current range selector, coupled between the timer and the current source, for outputting a first state of the current range signal while the measured pulse is outputted from the timer, and a second state of the current range signal while the measured pulse is not outputted from the timer, wherein responsive to the first state of the current range signal the current source provides the switch current at a first magnitude, and responsive to the second state of the current range signal the current source provides the switch current at a second magnitude.

2. A circuit in accordance with claim 1 wherein the second magnitude of the switch current is lower than the first magnitude of the switch current.

3. A circuit in accordance with claim 1 wherein the switch has an electrically conductive position and an electrically isolating position; and wherein the current source provides the switch current at the first magnitude while the switch is situated in the electrically isolating position with the current range signal in the first state, and provides the switch current at the second magnitude while the switch is situated in the electrically conductive position while the current range signal is in the second state.

4. A circuit in accordance with claim 3 wherein the second magnitude of the switch current is lower than the first magnitude of the switch current.

* * * * *